United States Patent
Deshpande et al.

(10) Patent No.: US 9,849,096 B2
(45) Date of Patent: Dec. 26, 2017

(54) NEUROPROTECTIVE EFFECT OF CAROTENOIDS IN BRAIN

(71) Applicant: OmniActive Health Technologies Limited, Thane W (IN)

(72) Inventors: Jayant Deshpande, Charlottetown (CA); J. Shankaranarayanan, Thane (IN)

(73) Assignee: OmniActive Health Technologies Limited, Thane (W) (IN)

( * ) Notice: Subject to any disclaimer, the term of this patent is extended or adjusted under 35 U.S.C. 154(b) by 0 days.

(21) Appl. No.: 14/780,595

(22) PCT Filed: Mar. 28, 2014

(86) PCT No.: PCT/IB2014/000447
§ 371 (c)(1),
(2) Date: Sep. 28, 2015

(87) PCT Pub. No.: WO2014/155189
PCT Pub. Date: Oct. 2, 2014

(65) Prior Publication Data
US 2016/0051490 A1   Feb. 25, 2016

(30) Foreign Application Priority Data
Mar. 28, 2013  (IN) .................. 1208/MUM/2013

(51) Int. Cl.
A61K 31/047  (2006.01)
A61K 31/07   (2006.01)
A61K 31/198  (2006.01)

(52) U.S. Cl.
CPC ............ *A61K 31/047* (2013.01); *A61K 31/07* (2013.01); *A61K 31/198* (2013.01)

(58) Field of Classification Search
CPC ..... A61K 31/047; A61K 31/07; A61K 31/198
See application file for complete search history.

(56) References Cited

U.S. PATENT DOCUMENTS

| | | | |
|---|---|---|---|
| 5,891,907 A | 4/1999 | Kolter et al. | |
| 2004/0022881 A1 | 2/2004 | Hauptmann et al. | |
| 2006/0205826 A1 | 9/2006 | Romero et al. | |

FOREIGN PATENT DOCUMENTS

| | | | | |
|---|---|---|---|---|
| CN | 102210662 | 10/2011 | | |
| EP | 0253490 A1 | * 1/1988 | ........... | A61K 9/2027 |
| EP | 1957057 | 8/2008 | | |
| EP | 2123263 | 11/2009 | | |
| IN | 2180MUM2007 | 6/2009 | | |
| WO | 9500130 | 1/1995 | | |
| WO | 2007067957 | 6/2007 | | |

OTHER PUBLICATIONS

Kitagawa et al., "Low-dose Levodopa Therapy in Japanese Patients with Parkinson's Disease: A Retrospective Study", Internal Medicine, vol. 44, No. 9, Sep. 2005, 5 ages 939-943.
Ravikrishnan et al., "Safety assessment of lutein and zeaxanthin (Lutemax TM 2020): Subchronic toxicity and mutagenicity studies", Food and Chemical Toxicology, vol. 49, 2011, pp. 2841-2848.
Deshpande, "Molecular dispersions of lipophilic nutrients in liquid hydrophilic carriers and process for preparation", Thomson Scientific, vol. 2009, No. 67, 2009, 2 pages.
Canfield et al., "Carotenoids as cellular antioxidants", Society for Experimental Biology and Medicine, vol. 200, 1992, pp. 260-265.
Thurnham, "Carotenoids: function and fallacies", Proceedings of the Nutrition Society, vol. 53, 1994, pp. 77-87.
Coleman, "Nutritional supplementation in age-related macular degeneration", Current Opinion in Ophthalmology, vol. 18, No. 3, 2007, pp. 220-223.
Billsten et al., "Photophysical Properties of Xanthophylls in Caroteno proteins from Human Retina", Photochemistry and Photobiology, vol. 78, No. 2, May 22, 2003, pp. 138-145.
Khachik et al., Isolation and Structure Elucidation of Geometric Isomers of Lutein, Zeaxanthin in Extracts of Human Plasma, Journal of Chromatography, vol. 582, 1992, pp. 153-166.
International Search Report and Written Opinion issued in the corresponding PCT application No. PCT/IB2014/000447, dated Aug. 1, 2014, 13 pages.

* cited by examiner

*Primary Examiner* — Sudhakar Katakam
(74) *Attorney, Agent, or Firm* — Hamre, Schumann, Mueller & Larson, P.C.

(57) ABSTRACT

The present invention provides use of composition containing molecular dispersions of carotenoids for the prevention of neurodegenerative disorders which are safe for human consumption and are particularly useful as dietary supplements for nutrition and health promoting benefits. The present invention particularly relates to the use of highly water soluble composition with enhanced bioavailability containing at least 80% by weight of total xanthophylls, out of which the trans-lutein content is 80-95% w/w; (R,R)-zeaxanthin is 14-20% w/w; (R,S)-zeaxanthin is 0.01-1% w/w and traces of other carotenoids derived from the plant extracts/oleoresin containing xanthophylls/xanthophylls esters. The present invention also provides use of the said composition in treatment of neurodegenerative disorders when co-administered along with reduced dose of Levodopa and Carbidopa.

3 Claims, No Drawings

NEUROPROTECTIVE EFFECT OF CAROTENOIDS IN BRAIN

FIELD OF THE INVENTION

The present invention relates to the use of a composition containing molecular dispersions of carotenoids for the management of neurodegenerative disorders. More particularly, the present invention relates to the use of a composition containing molecular dispersions of trans-lutein and zeaxanthin isomers namely (R,R)-zeaxanthin and (R,S)-zeaxanthin in a solid or liquid hydrophilic carrier, derived from plant extract/oleoresin containing xanthophylls/xanthophylls esters which are safe for human consumption and are particularly useful as dietary supplements for nutrition and health promoting benefits.

BACKGROUND OF THE INVENTION

The free radicals induced damage to mammalian tissues is believed to contribute the aging process and to the development of several degenerative diseases. (Canfiel LM et al. Carotenoids as cellular antioxidants. Proc Soc Exp Biol Med 1992; 200: 260-265).

The reactive free radicals react with polyunsaturated fatty acids (PUFA) of the membrane lipids and initiate the lipid peroxidation. The excessive lipid peroxidation caused by the free radicals leads to a condition of oxidative stress, which results in the accumulation of malondialdehyde (MDA). Oxidative stress leads to a variety of diseases.

Carotenoids are naturally occurring xanthophylls in plants that are involved in light harvesting reactions and protection of plant organelles against singlet oxygen induced damage. Dietary carotenoids serve as antioxidants in the tissues (Thurnham DL. Carotenoids: function and fallacies. Proc Nutr Soc 1994; 53: 77-87) and protect the body from oxidative damage. Mammalian species do not synthesize carotenoids and therefore these have to be obtained from dietary sources such as fruits and vegetables and or dietary supplements. Numerous epidemiological studies support a strong inverse relationship between consumption of carotenoid rich fruits and vegetables and incidence of degenerative diseases (Coleman H, Chew E. Nutritional supplementation in age-related macular degeneration. Curr Opin Ophthalmol 2007; 18(3): 220-223)

Xanthophylls can show both optical (R-and S-stereo isomers) and geometrical isomers (trans, E- and cis, Z-). The conformation of R- and S-stereo isomers is based on CD spectral and chiral column HPLC studies while the conformation of cis- and trans-isomers is based on electronic, infrared, NMR, HPLC-MS and HPLC-NMR on-line spectroscopy studies. It is well known that when an organic molecule has a carbon atom with four different types of atoms or groups attached to it, that carbon atom is designated as chiral carbon atom. The chiral carbon atom is responsible for two different spatial arrangements leading to the formation of optical isomers while the number of double bonds of the polyene chain and the presence of a methyl group and the absence of steric hindrance decide the number of trans- and cis-isomers. In the case of trans-zeaxanthin, the carbon atoms at 3 and 3' positions in the two end rings are both chiral atoms.

Thus, trans-zeaxanthin has two chiral centers at the carbon atoms C3 and C3', based on the positions of the secondary hydroxy groups attached to them. Therefore, there are four possible stereo isomers of trans-zeaxanthin namely, (3R-3'R)-isomer, (3S-3'S)-isomer and (3R-3'S)- or (3S-3'R)-isomer. In these isomers (3R-3'S)-& (3S-3'R)- are identical. Thus, there are three chiral isomers of trans-zeaxanthin. The isomer causing rotation of polarized light in a right handed manner is called R-stereo isomer, the isomer causing left handed rotation S-stereo isomer and the third isomer possessing a twofold opposite effects (R,S; optically inactive) which is called meso-form of zeaxanthin. The structural formulae of lutein, (R,R)-zeaxanthin and (R,S)-meso zeaxanthin are given below in Fig. 1

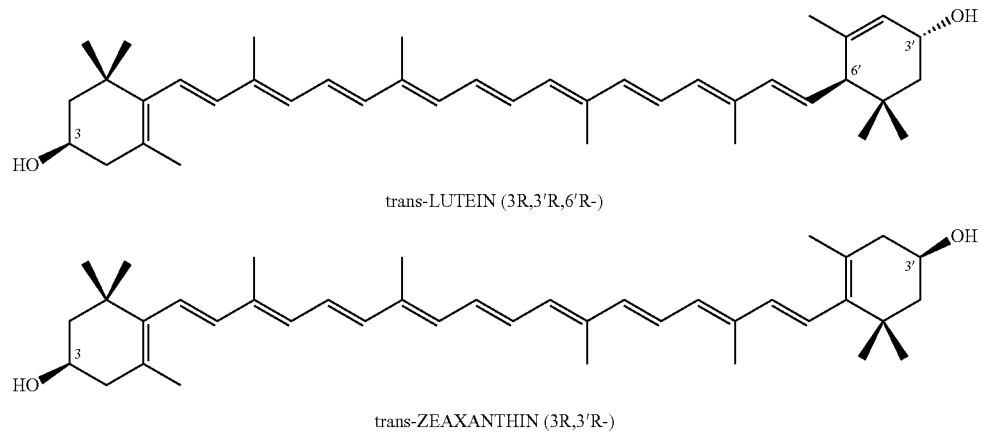

FIG. 1. Chemical structures of carotenoids trans-LUTEIN (3R,3'R,6'R-)

trans-ZEAXANTHIN (3R,3'R-)

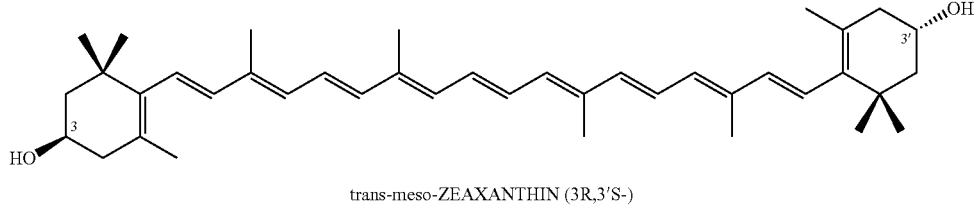

trans-meso-ZEAXANTHIN (3R,3'S-)

Lutein, (R,R)-zeaxanthin and (R,S)-zeaxanthin are the only macular carotenoids and due to their extended conjugated structure have been shown to produce significant antioxidant potential and protect the oxidative damage induced by singlet oxygen produced by ultra violet light. Intake of foods rich in lutein and zeaxanthin is related to increased level of these carotenoids in the serum as well as in the macula. Lutein and (R,R)-zeaxanthin can be derived from fruits and vegetables while (R,S)-zeaxanthin from sea foods or dietary supplements or from bio conversion of lutein within the body.

The conjugated double bonds of lutein and zeaxanthin contribute to the distinctive colors of each pigment, and also influence the ability of these to quench singlet oxygen. Due to the extra conjugated double bond, zeaxanthin is believed to be a stronger anti-oxidant compared to lutein.

Regarding the location of xanthophylls at a cellular level, they are reported to be bound to specific proteins referred to as xanthophylls binding protein (XBP). The XBP is suggested to be involved in the uptake of lutein and zeaxanthin from the blood stream and stabilization of the same in the retina. The study of xanthophylls and XBP by femto-second transient absorption spectroscopy showed better stability for (3R,3'S)-zeaxanthin enriched XBP compared to (3R,3'R)-zeaxanthin while the photo physical properties of the xanthophylls: (3R,3'R)-zeaxanthin and (3R,3'S,meso)-zeaxanthin are generally identical. It is likely that the meso-zeaxanthin is better accommodated with XBP wherein the protein protects the xanthophylls from degradation by free radicals. Thus, the complex may be a better antioxidant than the free xanthophylls, facilitating improved protection of ocular tissue from oxidative damages. (Billsten et al., Photophysical Properties of Xanthophylls in Caroteno proteins from Human Retina, Photochemistry and Photobiology, 78, 138-145, 2003)

Lutein and zeaxanthin occur naturally in trans-isomeric form in fruits, vegetables and flowers (marigold). Because of the processing conditions due to heat and light, a small percentage of trans-form is converted into cis-isomeric form. Therefore, the preferred bio-available form is trans-isomeric as evidenced from the data of geometric isomers compositional analysis of human plasma. (Khachik et al., Isolation and Structure Elucidation of Geometric Isomers of Lutein, Zeaxanthin in Extracts of Human Plasma, J. Chrom. 582, 153-156, 1992). In view of this, it is desirable to use the trans-isomeric form of lutein and zeaxanthin as (R,R)-(R, S)-in dietary supplements.

Neurodegenerative disorders are associated with progressive loss of structure or functions of neurons eventually leading to their death. Parkinson's disorder is the most common form of neurodegeneration. In Parkinson's, neurodegeneration occurs due to deposition of protein residues like alpha-synnuclein. This kind of abnormal deposition triggers oxidative stress and inflammatory reactions causing apoptosis and leading to neuronal cell death.

Parkinson's disorder is a cause of loss of dopaminergic neurons and characterized by rigidity, tremors, akinesia, tongue chewing and loss of cognitive function and memory loss after some period of time. The number of US cases of Parkinson's disorder was found to be 340,000 in 2005, and is predicted to rise to 610,000 by 2030.

Drugs available for Parkinson's disorder provide only symptomatic relief, but they cannot reverse or stop the progression of the disease. Various naturally occurring antioxidants like epigallocatechin gallate (green tea antioxidant) have shown promising activity in seizing the progression of disease. Hence, it is interesting to search the effects of naturally occurring antioxidants as nutritional supplement for preventive treatment of Parkinson's disorder.

The lipophilic nutrients are poorly absorbed if administered either as oil suspensions or as beadlets, which are the currently used forms. The main reason for poor absorption is their poor solubility in water. Due to their insolubility their bioavailability is very poor. Lipophilic nutrients have limited absorption in the body due to limited solubility in the gastrointestinal tract. Generally, the bioavailability of such nutrients is below 40%. The bioavailability can be enhanced by reducing the particle size, which in turn will enhance their efficiency of micellization. Dispersion of nutritional products at molecular level is generally regarded as a technique of reducing the particle size. Such molecular dispersions provide higher efficiency for micellization of nutrients in water and thereby increase the bioavailability.

The molecular dispersions of lipophilic nutrients can be obtained by dispersing the solution of lipophilic nutrient in a polar or non polar organic solvent certain water soluble hydrophilic solid or liquid carrier systems. Upon removal of solvent under vacuum, the resultant dispersion remains as a homogenous liquid or solid dispersions which is suitable for filling in to soft gel capsules or in to licaps, tablets, capsules and other oral solid or liquid preparations. Because of such dispersions, the absorption of lipophilic nutrients can be enhanced several folds. The said technology is protected by the Applicant under granted patent number IN253078.

PRIOR ART

Modern treatments are effective at managing the early motor symptoms of the disease, mainly through the use of Levodopa, Carbidopa and dopamine agonists. As the disease progresses and dopaminergic neurons continue to be lost, a point eventually arrives at which these drugs become ineffective at treating the symptoms and at the same time produce a complication called dyskinesia, marked by involuntary writhing movements. Diet and some forms of rehabilitation have shown some effectiveness at alleviating symptoms. Surgery and deep brain stimulation have been used to reduce motor symptoms as a last resort in severe cases where drugs are ineffective. Research directions include investigations into new animal models of the disease and of the potential usefulness of gene therapy, stem cell transplants and neuroprotective agents. Medications to treat non-movement-related symptoms of PD, such as sleep disturbances and emotional problems, also exist.

In Parkinson's disorder, research has revealed that oxidative stress and free radicals add to the deterioration of brain tissue. Low levels of glutathione have been found in those suffering from severe damaged brain tissue due to Parkinson's disorder. High levels of glutathione can slow the progression of brain tissue damage. Memory loss associated with Alzheimer's disease has been proven to slow with an elevated level of glutathione in the body. Alzheimer's disease is characterized by degeneration of brain nerve cells and shrinkage of brain tissue. While it is unclear whether oxidative damage is a cause or merely an effect of Alzheimer's, glutathione has been proven to slow down the progression of the disease.

Medicines that replace dopamine are the most effective treatment. These medicines are combinations of Levodopa, which breaks down in your body to form dopamine, and another chemical that ensures that the Levodopa reaches your brain. Dopamine replacement medicines can provide long-term improvement, although there are some side-effects such as feeling sick and tiredness. They can also cause long-term problems such as unwanted movements of your face and limbs (dyskinesia) and may become less reliable over time, with symptoms fluctuating suddenly—this is often called the 'on-off syndrome'. Examples of medicines include co-beneldopa and co-careldopa.

Medicines that mimic the action of dopamine (dopamine agonists) are commonly taken alone or together with Levodopa. Examples include pramipexole, ropinirole and rotigotine. These have side-effects such as feeling sick or sudden sleepiness, so your doctor will start you off at a low dose. If you have had Parkinson's disorder for a long time and have unpredictable 'off periods' you may be prescribed apomorphine, which is an injection.

Amantadine acts like a dopamine replacement medicine but works on different sites in your brain. It has few side-effects, but is only used in the early stages of the disease and has a limited effect so isn't a first choice drug.

The treatment of Parkinson's disorder for most patient entails long term exposure to multiple agents, including anticholinergics, levodopa, amantadine, dopamine receptor agonists, catechol-O-methyltransferase inhibitors, selegiline (deprenyl) and clozapine. Patients with Parkinson's disorder require medication for the control of the motor symptoms of their condition, for related medical or psychiatric symptoms of the disorder, and for concurrent medical problems, such as hypertension or cardiac disease.

All these agents may cause adverse effects. There is a potential for drug-drug interactions between different antiparkinsonian agents and between antiparkinsonian medication and the other drugs a patient may be taking. Clinicians caring for patients with Parkinson's disorder must be knowledgeable about the potential adverse effects and drug interactions of an expanding array of medications for this condition.

Numerous prior art references are available that provide compositions containing carotenoids used for the prevention/treatment of neurodegenerative diseases.

WO95/00130 demonstrates use of hydroxy carotenoids (HCA) for the manufacture of a medicament for the treatment of diseases having an oxygenation mechanism. The medicament has free radical scavenging mechanism on lipids, lipoproteins, proteins and DNA. The compounds of the invention are especially useful in the prevention or treatment of cardiovascular or cerebrovascular disease, cancer, diabetes, rheumatoid arthritis, Parkinson's disorder, Down's syndrome, Alzheimer's disease or cataracts or other age related changes and may be combined with e.g. aspirin. Hydroxy carotenoids used in preparing the medicament have poor solubility and bioavailability and therefore the action is minimal.

US20040022881A1 demonstrates use of mixed zeaxanthin esters extracted from the species Tagetes erecta. The concentrate contains about 20 percent or more mixed zeaxanthin esters. The composition is administered orally to treat or prevent free radical-mediated diseases.

U.S. Pat. No. 5,891,907 of Kolter et al demonstrated stable aqueous solubilizates suitable for parenteral administration, of carotenoids and vitamins or vitamin derivatives, in which the carotenoid and the water-insoluble vitamins are, with the aid of a nonionic emulsifier, in the form of a micellar solution. The carotenoids are beta-carotene, lycopene, astaxanthin, canthaxanthin, citranaxanthin, zeaxanthin, apocarotenol and apocarotenoic esters. Parenteral administration of carotenoids used for preventing effects for various diseases like atherosclerosis, Parkinson's disorder is painful to take injections daily.

EP1957057 A1 Samuel Lockwood F et al demonstrated the compositions comprising xanthophyll carotenoids, or analogs or derivatives of astaxanthin, lutein, zeaxanthin, lycoxanthin, lycophyll, or lycopene, the compositions being effective for the reduction or prevention of oxidative stress in a human subject. The formulation may include astaxanthin, lutein and/or zeaxanthin. Inhibiting, reducing or ameliorating systemic or target organ oxidative stress may reduce at least some of the pathological consequences associated with elevated systemic and/or target organ oxidative stress, such as, for example, cardiovascular disease (e.g., hypertension, atherosclerosis) and certain neurodegenerative conditions (e.g., Parkinson's disorder). The carotenoid analogs or carotenoid derivatives are water soluble but xanthophylls carotenoids are water insoluble. Carotenoid analogs or carotenoid derivatives are produced by medicinal/synthetic process.

Overcoming the difficulty of delivering therapeutic agents to specific regions of the brain presents a major challenge to treatment of most brain disorders. In its neuroprotective role, the blood-brain barrier (BBB) functions to hinder the delivery of many potentially important diagnostic and therapeutic agents to the brain. Therapeutic molecules and antibodies that might otherwise be effective in diagnosis and therapy do not cross the BBB in adequate amounts.

From above it is clear that there is a need to provide a technology which can overcome the difficulty of delivering the therapeutic/preventive agents for neurodegeneration through BBB and also, to prevent the adverse effects caused by these therapeutic agents by reducing the dose levels.

OBJECTIVES OF THE PRESENT INVENTION

The main objective of the present invention is to provide molecular dispersions of carotenoids which are useful for the management of neurodegenerative diseases and which is safe for human consumption and are particularly useful as dietary supplements for nutrition and health promoting benefits.

Another objective of the present invention is to provide molecular dispersions of trans-lutein and zeaxanthin isomers namely (RR)-zeaxanthin and (RS)-zeaxanthin in a solid or liquid hydrophilic carrier, derived from plant extract/oleoresin containing xanthophylls/xanthophylls esters which are useful for preventing neurodegenerative disorders such as Parkinson's disorder.

Yet another objective of the present invention is to provide molecular dispersions of xanthophyll composition containing at least 80% by weight of total xanthophylls, out of which the trans-lutein content is 80-95% w/w; (RR)-zeaxanthin is 14-20% w/w and (R,S)-zeaxanthin is 0.01-1% w/w and traces of other carotenoids derived from the plant extracts/oleoresin containing xanthophylls/xanthophylls esters which are useful for preventing neurodegenerative disorders such as Parkinson's disorder.

Still another objective of the present invention is to provide molecular dispersions of xanthophyll composition containing trans-lutein and zeaxanthin isomers namely (R,R)-zeaxanthin and (R,S)-zeaxanthin in a solid or liquid hydrophilic carrier, wherein the complex has higher antioxidant potential than the free xanthophylls and which are useful for preventing neurodegenerative disorders such as Parkinson's disorder.

Yet another objective of the present invention is to provide molecular dispersions of carotenoids which have higher efficiency for micellization which enhances the bioavailability resulting in increased levels of carotenoids in blood due to which these molecular dispersions cross the blood-brain barrier even with lower concentration of Lutein and are useful for preventing neurodegenerative disorders such as Parkinson's disorder.

Still another objective of the present invention is to use molecular dispersions of carotenoids in the treatment of Parkinson's disorder by co-administering along with reduced dose of Levodopa and Carbidopa.

Still another objective of the present invention is to provide molecular dispersions of carotenoids in solid or liquid hydrophilic carriers which have higher bioavailability.

Yet another objective is to provide the molecular dispersions of carotenoids which are prepared by using safe solvents (GRAS) and are suitable for human consumption, with minimum solvent residues.

SUMMARY OF THE INVENTION

The usefulness of the product is described herein below which is illustrative as shown in the examples and should not be construed to limit the scope of the present invention in any manner whatsoever.

Many studies have shown that the antioxidant potential of carotenoids is enhanced if meso-zeaxanthin is present. The present invention is based on our finding that, higher water solubility and bioavailability can be achieved if the carotenoids are dispersed in a water soluble hydrophilic liquid or solid carrier. These highly water soluble molecular dispersions of carotenoids with enhanced bioavailability having higher efficiency for micellization lead to increased levels of carotenoids in blood and hence cross the blood-brain barrier and scavenge the free radicals effectively. These molecular dispersions of carotenoids can be used in the treatment of Parkinson's disorder when co-administered along with reduced dose of Levodopa and Carbidopa.

Accordingly, the present invention provides molecular dispersions of carotenoids which are useful for the management of neurodegenerative disorders and which is safe for human consumption and are particularly useful as dietary supplements for nutrition and health promoting benefits.

According to another embodiment the present invention provides use of the composition containing molecular dispersions of carotenoids for the prevention of neurodegenerative disorders such as Parkinson's disorder, Down's syndrome, Alzheimer's disease, Amyotrophic lateral sclerosis, Huntington's disease. Cognitive disorders, Dementia.

According to yet another embodiment the present invention provides use of composition containing molecular dispersions of carotenoids in the treatment of Parkinson's disorder by co-administering along with reduced dose of Levodopa and Carbidopa.

The composition is administered in the range of 0.5 mg to 100 mg per day.

Levodopa and Carbidopa administered along with the composition are in the range of 25 mg to 75 mg per day and 6.25 mg to 25 mg per day, respectively.

The said composition comprises carotenoids; stabilizer; water soluble hydrophilic carrier and optionally a surfactant.

The said composition contains at least 80% by weight of total xanthophylls, out of which the trans-lutein content is 80-95% w/w; (R,R)-zeaxanthin is 14-20% w/w; (R,S)-zeaxanthin is 0.01-1% w/w and traces of other carotenoids derived from the plant extracts/oleoresin containing xanthophylls/xanthophylls esters.

The stabilizer used is selected from Ascorbic acid, BHA, BHT, ascorbyl palmitate, rosemary extract, mixed natural tocopherols, alpha tocopheryl acetate, sodium ascorbate, castor oil derivatives, sodium lauryl sulfate and mixtures thereof.

The carrier used is selected from polyethylene glycol 200, polyethylene glycol 400, ethylene glycol, propylene glycol, glycerol, sorbitol, glucose syrup, corn steep liquor, mannitol, polyethylene glycol 6000, polyethylene glycol 10000, Polyethylene glycol 20000, polyvinyl pyrrolidone, hydroxyl propyl methyl cellulose, sucrose, glucose, sodium chloride, hydroxyl propyl cellulose, polyvinyl alcohol, soluble starch, hydrolyzed starch and mixtures thereof.

The said surfactant is selected from a group comprising of polysorbate 20, polysorbate 60, polysorbate 80, lecithin, sucrose fatty acid esters, glyceryl fatty acid esters, sodium lauryl sulfate and mixtures thereof.

The said dispersions are in the form of powders, tablets, capsules, sachets, beadlets, microencapsulated powders, oil suspensions, liquid dispersions, pellets, soft gel capsules, chewable tablets or liquid preparations.

It may be noted that a novel feature of the present invention is the use of molecular dispersions of trans-lutein and zeaxanthin isomers namely (R,R)-zeaxanthin and (R,S)-zeaxanthin in a solid or liquid hydrophilic carrier with enhanced water solubility and bioavailability which helps in effectively delivering the molecules across the blood-brain barrier and shows potential in prevention/treatment of the neurodegenerative disorders such as Parkinson's disorder. The use of this combination of carotenoids having higher antioxidant potential in highly water soluble form with enhanced bioavailability for prevention/treatment of Parkinson's disorder has not been reported in the prior art.

DESCRIPTION OF THE INVENTION

Neurodegenerative disorders are associated with progressive loss of structure or functions of neurons eventually leading to their death. Parkinson's disorder is the most common form of neurodegeneration. Antioxidant compounds are considered to have high antioxidant potential in the prevention of many human ailments such as age related macular degeneration cataract and neurodegenerative diseases. Various naturally occurring antioxidants like epigallocatechin gallate (green tea antioxidant) have shown promising activity in seizing the progression of disease.

Lutein is a naturally occurring antioxidant found in green leafy vegetables like spinach. Lutein is also found in eye mainly present in macula lutea. It is well known that lutein is a carotenoid and powerful antioxidant. It has been used in cataracts and macular degeneration which is an age related degenerative disorder. Lutein has also shown protective antioxidant activity in human HepG2 cell lines.

Zeaxanthin is one of the most common carotenoid alcohols found in nature. Lutein and zeaxanthin have identical chemical formulas and are isomers, but they are not stereoisomers. The only difference between them is in the location of the double bond in one of the end rings. This difference gives lutein three Chiral centers whereas zeaxanthin has two. Because of symmetry, the (3R,3'S) and (3S,3'R) stereoisomers of zeaxanthin are identical. Therefore, zeaxanthin has only three stereoisomeric forms. The (3R,3'S) stereoisomer is called meso-zeaxanthin.

The conjugated double bonds of lutein and zeaxanthin contribute to the distinctive colors of each pigment, and also influence the ability of these to quench singlet oxygen. Due to the extra conjugated double bond, zeaxanthin is believed to be a stronger anti-oxidant compared to lutein. It has been demonstrated that the complex of lutein and zeaxanthin isomers act as a better antioxidant than the free xanthophylls, facilitating improved protection from oxidative damages.

The lipophilic nutrients are poorly absorbed if administered either as oil suspensions or as beadlets, which are the currently used forms. The main reason for poor absorption is their poor solubility in water. Due to their insolubility their bioavailability is very poor. Dispersion of nutritional products at molecular level provides higher efficiency for micellization of nutrients in water and thereby increases the bioavailability.

The present invention therefore provides use of carotenoids composition containing at least 80% by weight of total xanthophylls, out of which the trans-lutein content is 80-95% w/w; (R,R)-zeaxanthin is 14-20% w/w and (R,S)-zeaxanthin is 0.01-1% w/w and traces of other carotenoids derived from the plant extracts/oleoresin containing xanthophylls/xanthophylls esters in highly water soluble form with enhanced bioavailability in alleviating the symptoms of Parkinson's disorder.

Studies with rats were carried out to test the anti-Parkinson's activity of three samples viz water soluble composition of trans-lutein and zeaxanthin isomers (sold under the brand name UltraSol Lutemax2020™); concentrate containing trans-lutein and zeaxanthin isomers (sold under the brand name Lutemax2020®) and concentrate containing high content of trans-lutein and/or zeaxanthin (sold under the brand name Lutemax®).

From the preliminary studies it was found that the water soluble composition of trans-lutein and zeaxanthin isomers which contains 2.5 mg of Lutein exhibited better anti-parkinson's activity and hence this composition was used to test further the effect of the said composition when co-administered with the drugs Levodopa and Carbidopa which are used in the treatment of Parkinson's disorder.

The following examples are given by the way of illustration of the present invention and therefore should not be construed to limit the scope of the present invention.

Parkinson's disorder was induced in Wistar rats by haloperidol and rotenone. Haloperidol induces catalepsy and rotenone induces loss of dopaminergic activity in rats.

EXAMPLE 1

Pharmacological Evaluation of Lutein Using Haloperidol Model of Parkinson's Disease Animals: Male Wistar rats procured from Hafikines institute were used for the study. They were acclimatized in the animal house of Bombay College of Pharmacy. Animals were fed standard diet and 12 hours light/dark cycle was maintained.

Chemicals: Haloperidol (Serenace inj. 5 mg/ml, RPG Life sciences), Sodium Carboxy methyl cellulose (Thomas Baker). All the solvents used were of AR grade and obtained from S.D. fine Chem.

Methods:

Rats (180-220 gm) were randomly selected and grouped into the following groups of 6 animals of each.

Group I: Positive control (PC)—Diseased Animal (Haloperidol 1.25 mg/kg)
Group II: Normal control (NC)—Normal Animal (Vehicle)
Group A1: Water soluble composition of trans-lutein and zeaxanthin isomers (50 mg containing 2.5 mg of Lutein)
Group A2: Water soluble composition of trans-lutein and zeaxanthin isomers (100 mg containing 5 mg of Lutein)
Group B1: Concentrate containing trans-lutein and zeaxanthin isomers (50 mg containing 33 mg of Lutein)
Group B2: Concentrate containing trans-lutein and zeaxanthin isomers (100 mg containing 66 mg of Lutein)
Group C1: Concentrate containing high content of trans-lutein and/or zeaxanthin (50 mg containing 35.5 mg of Lutein)
Group C2: Concentrate containing high content of trans-lutein and/or zeaxanthin (100 mg containing 71 mg of Lutein)
Group D: Levodopa 75 mg/kg+Carbidopa 25 mg/kg.
Group E: Water soluble composition of trans-lutein and zeaxanthin isomers (50 mg/kg containing 2.5 mg Lutein i.e. 5% Lutein).
Group F1: Levodopa 75 mg/kg+Carbidopa 25 mg/kg+5% Lutein (50 mg containing 2.5 mg Lutein).
Group F2: Levodopa 50 mg/kg+Carbidopa 12.5 mg/kg+5% Lutein (50 mg containing 2.5 mg Lutein).
Group F3: Levodopa 25 mg/kg+Carbidopa 6.25 mg/kg+5% Lutein (50 mg containing 2.5 mg Lutein).

The doses of 50 mg/kg and 100 mg/kg were prepared by suspending the test compounds in 0.5% aqueous sodium CMC.

Haloperidol Induced Catalepsy: Test drugs were administered in appropriate doses mentioned above and one hour after the drug administration animals were challenged with Haloperidol 1.25 mg/kg i.p. This dosing regimen was continued for 21 days and behavioral assessments were done at seven-day interval i.e. 1st, 7th, 14th and 21st day. On 21st day, animals were sacrificed after the behavioral study; brains were removed and used for monoamine estimations.

Following tests were carried out to assess behavioral activity:

Standard Bar Test:

The rat forepaws were placed on a 12 cm high horizontal bar located in a sound attenuated area with background white (static) noise. Catalepsy was measured for 3 min and each animal underwent three consecutive trials with 5-10 min break between the tests. An animal was considered cataleptic if both forepaws remained on the bar for at least 1 min. Catalepsy score (immobility time in seconds) of each animal was analyzed by calculating mean scores (Mandhane et al 1997).

Actophotometer:

The locomotor activity was evaluated by using Actophotometer. Actophotometer consists of a plexiglass cage (30×23×22 cm). Rats were introduced in this cage and activity was recorded for five min after allowing the rats to adapt to the new environment for few minutes. An array of photoelectric beam emitter pairs (spaced at 2.65 cm intervals) measured the animal activity along a single axis of motion; the ambulation was expressed in terms of total photo beam counts/5 min/animal. (Mandhane et al 1997).

Elevated Plus Maze:

Transfer latency that is the latency to enter into closed arm from open arm was calculated. Maximum time given to each animal was 90 seconds. This was done in elevated plus maze consisting of two open and two closed arms (Mandhane et al 1997).

Monoamine Estimations:

On the 21st day, after the behavioral studies the animals were sacrificed and brains were removed. In case of monoamine estimation the brains were weighed and homogenized in acidified butanol in a Teflon homogenizer and centrifuged. Further supernatant was removed and Dopamine (Schmidt, 1958), Norepinephrine (Shore et. al 1957) and 5-Hydroxytryptamine (Bogdanski et. al 1955) were extracted using heptane.

Statistical Analysis: Mean and standard error of mean was calculated. Analysis of variance ANOVA was applied to the data followed by Dunnet's test as a post test. Graph pad Prism version 5.0 was used for statistical analysis.

Behavioral Studies:

Effect of lutein and combination treatments on catalepsy was measured using standard bar test. Test was done at ten days interval. All values are expressed in cataleptic time in seconds. Following are the results of bar test:

| Sr. No. | Group | \ | \ | Time Intervals in Minutes | \ | \ | \ |
|---|---|---|---|---|---|---|---|
| | | 0 | 30 | 60 | 120 | 180 | 240 |
| | | | | Catalepsy in Seconds | | | |
| | | | | DAY 1 | | | |
| 1 | NC | 1.17 ± 0.17 | 1.37 ± 0.52 | 0.77 ± 0.26 | 1.52 ± 0.66 | 2.89 ± 1.06 | 1.93 ± 0.27 |
| 2 | PC | 1.64 ± 0.50 | 16.05 ± 1.39* | 76.47 ± 17.36* | 148.08 ± 11.16* | 166.90 ± 11.49* | 168.0 ± 10.33* |
| 3 | A1 | 0.74 ± 0.15 | 6.29 ± 0.79** | 10.85 ± 1.92** | 14.25 ± 1.25** | 18.68 ± 3.37** | 22.60 ± 3.84** |
| 4 | A2 | 0.89 ± 0.71 | 14.77 ± 2.53 | 16.64 ± 2.43** | 14.43 ± 1.35** | 31.68 ± 4.86** | 27.81 ± 4.48** |
| 5 | B1 | 0.72 ± 0.72 | 11.51 ± 1.35 | 11.86 ± 2.41** | 17.49 ± 11.32** | 38.52 ± 0.73** | 24.42 ± 5.70** |
| 6 | B2 | 0.13 ± 0.13 | 14.79 ± 2.051 | 13.38 ± 0.59** | 25.89 ± 5.99** | 13.46 ± 1.84** | 21.65 ± 2.87** |
| 7 | C1 | 2.91 ± 0.80 | 3.30 ± 0.62** | 18.85 ± 3.61** | 33.30 ± 10.48** | 17.45 ± 1.032** | 18.37 ± 1.68** |
| 8 | C2 | 1.32 ± 0.45 | 8.715 ± 2.79** | 23.43 ± 7.14** | 14.07 ± 2.18** | 25.57 ± 9.19** | 28.23 ± 6.95** |
| 9 | D | 0.49 ± 0.11 | 1.8 ± 0.13** | 1.8 ± 0.07** | 2.12 ± 0.17** | 3.69 ± 0.58** | 5.3 ± 0.59** |
| 10 | E | 0.49 ± 0.07 | 0.8 ± 0.26** | 1.01 ± 0.15** | 0.83 ± 0.16** | 0.68 ± 0.16** | 0.89 ± 0.19** |
| 11 | F1 | 1.05 ± 0.15 | 1.72 ± 0.17** | 1.67 ± 0.05** | 1.81 ± 0.24** | 6.0 ± 1.0** | 7.34 ± 0.59** |
| 12 | F2 | 0.90 ± 0.17 | 1.64 ± 0.07** | 7.98 ± 0.87** | 13.20 ± 0.46** | 16.84 ± 0.87** | 17.37 ± 1.33** |
| 13 | F3 | 0.77 ± 0.122 | 1.98 ± 0.23** | 9.6 ± 0.60** | 12.2 ± 0.54** | 17.7 ± 0.74** | 16.17 ± 0.9** |
| | | | | DAY 7 | | | |
| 14 | NC | 1.74 ± 0.18 | 2.56 ± 0.97 | 2.32 ± 0.34 | 1.83 ± 0.33 | 1.70 ± 0.24 | 3.60 ± 1.48 |
| 15 | PC | 3.7 ± 1.00 | 40.34 ± 8.46* | 63.42 ± 5.44* | 148.49 ± 15.96* | 164.46 ± 13.26* | 159.64 ± 10.21* |
| 16 | A1 | 5.42 ± 1.57 | 15.26 ± 4.89** | 15.03 ± 1.45** | 14.43 ± 2.94** | 22.99 ± 3.61** | 15.31 ± 0.83** |
| 17 | A2 | 4.05 ± 1.26 | 15.06 ± 4.50** | 16.16 ± 2.47** | 18.64 ± 2.05** | 19.06 ± 0.642** | 23.99 ± 8.26** |
| 18 | B1 | 1.97 ± 0.81 | 13.59 ± 2.40** | 13.19 ± 3.28** | 13.54 ± 3.25** | 19.93 ± 4.66** | 14.27 ± 3.36** |
| 19 | B2 | 3.23 ± 0.37 | 19.31 ± 3.62** | 22.86 ± 8.41 | 16.25 ± 1.50** | 13.50 ± 3.38** | 18.44 ± 0.98** |
| 20 | C1 | 3.28 ± 0.76 | 28.04 ± 8.99** | 23.96 ± 9.22** | 8.12 ± 2.09** | 14.77 ± 2.50** | 28.37 ± 9.68 |
| 21 | C2 | 1.45 ± 0.37 | 8.35 ± 1.06** | 20.37 ± 6.34** | 14.26 ± 0.35** | 19.63 ± 2.35** | 28.17 ± 2.49** |
| 22 | D | 0.62 ± 0.11** | 1.57 ± 0.06** | 2.3 ± 0.32** | 2.77 ± 0.37** | 3.54 ± 0.31** | 4.4 ± 1.16** |
| 23 | E | 0.90 ± 0.14** | 0.42 ± 0.11** | 0.45 ± 0.08** | 0.37 ± 0.1** | 0.88 ± 0.34** | 0.76 ± 0.11** |
| 24 | F1 | 0.57 ± 0.165** | 1.86 ± 0.186** | 2.45 ± 0.29** | 2.52 ± 0.27** | 4.43 ± 0.85** | 8.96 ± 1.0** |
| 25 | F2 | 0.74 ± 0.24** | 2.47 ± 0.25** | 11.12 ± 1.69** | 11.90 ± 2.01** | 18.39 ± 1.49** | 17.19 ± 2.21** |
| 26 | F3 | 1.14 ± 0.28 | 1.74 ± 0.24** | 12.27 ± 1.34** | 13.68 ± 2.12** | 14.05 ± 1.78** | 17.83 ± 1.14** |
| | | | | DAY 14 | | | |
| 27 | NC | 1.22 ± 0.13 | 1.87 ± 0.37 | 1.76 ± 0.26 | 2.68 ± 1.05 | 1.59 ± 0.23 | 2.99 ± 0.72 |
| 28 | PC | 4.82 ± 1.51 | 21.35 ± 0.39* | 80.72 ± 4.78* | 148.50 ± 12.54* | 145.32 ± 10.47* | 162.25 ± 12.88* |
| 29 | A1 | 2.43 ± 0.94 | 9.43 ± 0.75** | 22.62 ± 2.71** | 16.88 ± 1.59** | 11.58 ± 2.76** | 13.55 ± 3.33** |
| 30 | A2 | 3.27 ± 1.33 | 14.27 ± 1.75** | 23.17 ± 3.99** | 26.39 ± 5.18** | 23.83 ± 2.61** | 31.77 ± 0.39** |
| 31 | B1 | 2.44 ± 0.67 | 13.52 ± 0.82** | 33.78 ± 0.52** | 26.71 ± 4.60** | 33.83 ± 7.82** | 54.74 ± 1.88** |
| 32 | B2 | 4.03 ± 0.96 | 26.25 ± 3.17** | 56.84 ± 5.06** | 38.16 ± 7.75** | 37.75 ± 9.15** | 49.24 ± 8.13 |
| 33 | C1 | 4.04 ± 0.75 | 16.04 ± 2.48** | 22.00 ± 3.13** | 30.54 ± 6.85** | 34.36 ± 5.06** | 17.75 ± 3.56** |
| 34 | C2 | 2.34 ± 0.15 | 7.21 ± 2.81** | 19.41 ± 4.79** | 33.15 ± 6.45** | 52.09 ± 3.58** | 38.62 ± 6.79** |
| 35 | D | 0.88 ± 0.18** | 1.92 ± 0.14** | 2.86 ± 0.83** | 3.54 ± 0.23** | 4.94 ± 1.21** | 5.87 ± 1.30** |
| 36 | E | 0.54 ± 0.17** | 0.50 ± 0.08** | 0.58 ± 0.10** | 0.64 ± 0.18** | 0.65 ± 0.29** | 0.68 ± 0.29** |
| 37 | F1 | 1.12 ± 0.26** | 2.33 ± 0.38** | 3.91 ± 1.0** | 5.26 ± 1.45** | 4.72 ± 1.32** | 5.71 ± 1.13** |
| 38 | F2 | 0.66 ± 0.18** | 8.52 ± 0.73** | 13.51 ± 1.0** | 16.18 ± 1.9** | 18.09 ± 1.26** | 18.40 ± 2.0** |
| 39 | F3 | 0.93 ± 0.32** | 10.52 ± 0.63** | 16.94 ± 1.31** | 15.61 ± 2.33** | 17.48 ± 2.02** | 15.42 ± 1.68** |
| | | | | DAY 21 | | | |
| 40 | NC | 2.76 ± 1.03 | 1.60 ± 0.11 | 2.37 ± 0.42 | 2.39 ± 0.10 | 2.33 ± 0.24 | 2.02 ± 0.43 |
| 41 | PC | 4.92 ± 1.35 | 23.04 ± 2.51* | 153.25 ± 11.60* | 174.50 ± 3.20* | 174.25 ± 4.25* | 178.50 ± 1.190* |
| 42 | A1 | 1.88 ± 0.29 | 8.65 ± 1.14** | 12.71 ± 0.68** | 13.79 ± 0.72** | 16.05 ± 0.58** | 18.69 ± 1.46** |
| 43 | A2 | 2.63 ± 0.94 | 10.58 ± 1.67** | 14.02 ± 0.93** | 14.98 ± 1.64** | 18.59 ± 1.39** | 18.08 ± 0.82** |
| 44 | B1 | 3.51 ± 0.80 | 10.47 ± 0.84** | 15.14 ± 1.15** | 18.17 ± 1.22** | 25.89 ± 4.20** | 21.78 ± 3.30** |
| 45 | B2 | 3.12 ± 0.97 | 12.62 ± 1.69** | 18.74 ± 1.14** | 20.93 ± 0.33** | 40.20 ± 12.30 | 29.17 ± 3.32** |
| 46 | C1 | 2.11 ± 0.27 | 12.76 ± 0.64** | 21.83 ± 0.56** | 22.34 ± 4.14** | 25.30 ± 3.46** | 21.79 ± 4.70** |

-continued

| Sr. No. | Group | \multicolumn{6}{c}{Time Intervals in Minutes} | | | | | |
|---|---|---|---|---|---|---|---|
| | | 0 | 30 | 60 | 120 | 180 | 240 |
| 47 | C2 | 2.14 ± 0.73 | 13.10 ± 0.52** | 15.76 ± 1.41** | 20.68 ± 0.87** | 15.02 ± 1.75** | 18.69 ± 1.04** |
| 48 | D | 1.22 ± 0.24** | 3.14 ± 0.41** | 2.8 ± 0.55** | 3.25 ± 0.56** | 3.09 ± 0.90** | 5.13 ± 1.09** |
| 49 | E | 1.61 ± 0.12** | 0.74 ± 0.27** | 0.94 ± 0.27** | 2.34 ± 0.24** | 1.31 ± 0.33** | 1.85 ± 0.37** |
| 50 | F1 | 0.89 ± 0.21** | 5.27 ± 0.92** | 2.95 ± 0.50** | 4.59 ± 1.17** | 4.64 ± 0.85** | 4.59 ± 1.16** |
| 51 | F2 | 1.26 ± 0.38** | 10.03 ± 0.80** | 16.75 ± 1.43** | 17.98 ± 1.30** | 18.24 ± 1.46** | 17.7 ± 1.67** |
| 52 | F3 | 0.92 ± 0.27** | 8.14 ± 1.80** | 19.78 ± 1.54** | 17.59 ± 3.02** | 20.60 ± 1.45** | 18.21 ± 2.0 |

Data represents mean ± SEM (n = 10). One way ANOVA followed by Dunnett's test. ($P < 0.05$).
*Positive control group was found to be significantly different from the negative control group.
**Treatment groups were found to be significantly ($P < 0.05$) different from positive control group.

Locomotor Activity

| Sr. No. | Group Days | Mean ± SEM Day 5 | Mean ± SEM DAY 10 | Mean ± SEM Day 15 | Mean ±S EM Day 20 |
|---|---|---|---|---|---|
| 1 | NC | 250.75 ± 27.20 | 254.25 ± 22.42 | 266 ± 29.93 | 203.25 ± 21.25 |
| 2 | PC | 66.75 ± 7.89* | 62.5 ± 9.38* | 62.25 ± 9.93* | 54.75 ± 4.19* |
| 3 | A1 | 71.75 ± 9.59 | 97.5 ± 8.93 | 80.5 ± 13.44 | 121.5 ± 6.64** |
| 4 | A2 | 74.25 ± 6.81 | 101 ± 4.98 | 122.75 ± 25.16 | 144.75 ± 9.93** |
| 5 | B1 | 73.00 ± 9.41 | 150.5 ± 11.44 | 125 ± 36.13 | 164.75 ± 20** |
| 6 | B2 | 107.25 ± 29.46 | 134.75 ± 33.93 | 185 ± 48.20 | 140.5 ± 15.11** |
| 7 | C1 | 74.5 ± 6.11 | 130.5 ± 41.18 | 131.75 ± 23.63 | 194.7 ± 9.55** |
| 8 | C2 | 109.25 ± 27.66 | 133 ± 21.81 | 152 ± 19.48 | 168 ± 10.59** |
| 9 | NC | 479.5 ± 10.57 | 502.83 ± 6.0 | 510.50 ± 8.04 | 508.83 ± 13.91 |
| 10 | PC | 153 ± 12.54* | 122.66 ± 6.2* | 134.33 ± 5.31* | 137.50 ± 3.47* |
| 11 | D | 506.33 ± 6.302** | 501.66 ± 7.93** | 486.50 ± 14.68** | 502.50 ± 11.69** |
| 12 | F | 485.31 ± 8.47** | 499.66 ± 6.07** | 512.33 ± 15.98** | 491.16 ± 12.82** |
| 13 | F1 | 456 ± 16.32** | 452.66 ± 10.14** | 492.33 ± 8.77** | 514.83 ± 8.73** |
| 14 | F2 | 364 ± 10.56** | 402.83 ± 24.66** | 315.50 ± 9.94* | 327.33 ± 7.32** |
| 15 | F3 | 403.167 ± 8.82** | 420 ± 11.63** | 381.00 ± 14.63** | 331.00 ± 18.61** |

Data represents mean ± SEM of ambulation counts (n = 10). One way ANOVA followed by Dunnett's test, Evaluation was done at every five-day interval and counts were measured for five minutes for each animal.
*Positive Control group was found to be significantly ($P < 0.05$) different than negative control group.
**Treatment groups were found to be significantly ($P < 0.05$) different than positive control group.

Evaluation of Cognitive Function by Transfer Latency

| Sr No. | Treatment Groups | Mean ± SEM |
|---|---|---|
| 1 | NC | 26.49 ± 1.32 |
| 2 | PC | 90 ± 0.0* |
| 3 | A1 | 43.57 ± 4.55** |
| 4 | A2 | 37.24 ± 5.38** |
| 5 | B1 | 48.11 ± 5.18** |
| 6 | B2 | 59.47 ± 17.77 |
| 7 | C1 | 44.53 ± 15.27** |
| 8 | C2 | 43.82 ± 5.08** |
| 9 | D | 43.01 ± 2.08 |
| 10 | E | 44.47 ± 2.77 |
| 11 | F1 | 46.81 ± 1.76 |
| 12 | F2 | 44.61 ± 2.94 |
| 13 | F3 | 47.56 ± 1.92 |

Data represents mean ± SEM of transfer latency in secs. (n = 10). One way ANOVA followed by Dunnett's test,
*Positive Control group was found to be significantly ($P < 0.05$) different than negative control group.
**Treatment groups were found to be significantly ($P < 0.05$) different than positive control group.

Biochemical Estimations

Effect of Various Treatment Groups on the Brain Levels of Monoamines:

Monoamine viz. Dopamine. Norepinephrine, 5-Hydroxytryptamine levels in brain were estimated at the end of the study. Animals were sacrificed and brains were removed to estimate the levels of neurotransmitters. All values are expressed in μg/g of brain weight.

| Groups | Dopamine Mean ± SEM | Norepinephrine Mean ± SEM | 5-Hydroxytryptamine Mean ± SEM |
|---|---|---|---|
| NC | 0.97 ± 0.01 | 0.6 ± 0.05 | 0.58 ± 0.01 |
| PC | 0.38 ± 0.01* | 0.23 ± 0.03* | 0.17 ± 0.02* |
| A1 | 0.94 ± 0.02** | 0.68 ± 0.01** | 0.46 ± 0.02** |
| A2 | 0.79 ± 0.02** | 0.61 ± 0.02** | 0.42 ± 0.03** |
| B1 | 0.62 ± 0.05** | 0.51 ± 0.01** | 0.52 ± 0.02** |
| B2 | 0.63 ± 0.05** | 0.55 ± 0.04** | 0.24 ± 0.02** |
| C1 | 0.85 ± 0.01** | 0.56 ± 0.02** | 0.52 ± 0.03** |
| C2 | 0.75 ± 0.02** | 0.51 ± 0.01** | 0.43 ± 0.03** |
| D | 0.82 ± 0.04** | 0.38 ± 0.0 | 0.21 ± 0.08 |
| E | 0.89 ± 0.02** | 0.54 ± 0.04** | 0.5 ± 0.04** |
| F1 | 0.92 ± 0.07** | 0.58 ± 0.01** | 0.67 ± 0.07** |
| F2 | 0.85 ± 0.02** | 0.62 ± 0.03** | 0.52 ± 0.04** |
| F | 0.79 ± 0.04** | 0.55 ± 0.02** | 0.6 ± 0.02** |

Data represents mean ± SEM (n = 6). One way ANOVA followed by Dunnett's test, $P < 0.05$,
*Positive control group was found to be significantly different from the negative control group.
**Treatment groups were found to be significantly different from positive control group.

EXAMPLE 2

Pharmacological Evaluation of Lutein Using Rotenone Model of Parkinson's Disease Materials:

Animals: Male wistar rats procured from Haffkines institute were used for the study. They were acclimatized in the animal house of Bombay College of Pharmacy. Animals were fed standard diet and 12 hours light/dark cycle was maintained.

Chemicals: Rotenone (Sigma Aldrich) Sodium Carboxy methyl cellulose (Thomas Baker). All the solvents used were of AR grade and obtained from S.D. fine Chem.

Groups:
Rats (180-220 gm) were randomly selected and grouped into the following groups of 6 animals of each.
Group I: Positive control (PC) (Rotenone, 2 mg/kg)
Group II: Normal control (NC) (Vehicle)
Group A1: Water soluble composition of trans-lutein and zeaxanthin isomers (50 mg containing 2.5 mg of Lutein)
Group A2: Water soluble composition of trans-lutein and zeaxanthin isomers (100 mg containing 5 mg of Lutein)
Group B1: Concentrate containing trans-lutein and zeaxanthin isomers (50 mg containing 33 mg of Lutein)
Group B2: Concentrate containing trans-lutein and zeaxanthin isomers (100 mg containing 66 mg of Lutein)
Group C1: Concentrate containing high content of trans-lutein and/or zeaxanthin (50 mg containing 35.5 mg of Lutein)
Group C2: Concentrate containing high content of trans-lutein and/or zeaxanthin (100 mg containing 71 mg of Lutein)

The doses of 50 mg/kg and 100 mg/kg were prepared by suspending the test compounds in 0.5% aqueous sodium CMC. Control animals received equal volume of appropriate vehicle.

Rotenone Induced Parkinson's Disorder: Test drugs were administered in appropriate doses mentioned above and one hour after the drug administration animals were challenged with rotenone 2 mg/kg i.p. This dosing regimen was continued for 24 days and behavioral assessments of catalepsy were done at ten days interval i.e. 1st, 10th, and 20th. Locomotor activity was evaluated at five days interval. On 24th day, animals were sacrificed after the behavioral study: brains were removed and brain monoamine estimations were done.

Following tests were carried out to assess behavioral activity:

Effect of Lutein on Locomotor Activity Using Digital Actophotometer: Results are expressed in ambulation counts. Evaluation was done at every five-day interval and counts were measured for five minutes for each animal.

Effect of Lutein on Locomotor Activity

| Sr. No | Days Groups | 5th Day Mean ± SEM | 10th Day Mean ± SEM | 15th Day Mean ± SEM | 20th Day Mean ± SEM |
|---|---|---|---|---|---|
| 1 | NC | 453.25 ± 33.07 | 493.12 ± 57.93 | 494.37 ± 29.59 | 68.12 ± 6.35* |
| 2 | PC | 476.25 ± 28.37 | 424.12 ± 51.31 | 171 ± 24.49* | 283 ± 41.62** |
| 3 | A1 | 478.25 ± 38.07 | 477.5 ± 35.02 | 441.5 ± 26.65** | 410 ± 29.74** |
| 4 | A2 | 443.12 ± 53.61 | 510.62 ± 36.50 | 501.12 ± 41.50** | 351.62 ± 9.52** |
| 5 | B1 | 479.25 ± 10.74 | 455.50 ± 15.40 | 67.50 ± 12.37** | 364.75 ± 17.39** |
| 6 | B2 | 474.37 ± 13.44 | 446.62 ± 15.07 | 446.37 ± 10.55** | 407.25 ± 23.55** |
| 7 | C1 | 471.625 ± 8.02 | 449.25 ± 11.40 | 398.50 ± 1850** | 376.75 ± 21.54** |
| 8 | C2 | 474.37 ± 4.49 | 437.62 ± 10.42 | 424.75 ± 17.08** | 519.87 ± 31.34** |

Data represents mean ± SEM (n =8 of ambulation counts. One way ANOVA followed by Dunnett's test, P < 0.05,
*Positive control group was found to be significantly different than negative control group and
**Treatment groups were found to be significantly different than positive control group. There was significant difference between A1 and C1 treated groups at 20th day.

Effect of Lutein on Memory and Cognitive Function: The effect was evaluated using elevated plus maze. Transfer latency i.e. latency to enter into closed arm was measured to evaluate the memory function. All results are expressed in seconds.

Effect of Lutein on Transfer Latency

| Treatment Groups | Mean ± SEM |
|---|---|
| Negative Control | 10.61 ± 0.64 |
| Positive Control | 79.28 ± 4.45* |
| A1 | 25.96 ± 4.76** |
| A2 | 35.74 ± 8.95** |
| B1 | 32.79 ± 4.87** |
| B2 | 26.55 ± 1.40** |
| C1 | 33.69 ± 1.06** |
| C2 | 24.91 ± 1.26 |

Data represents mean ± SEM (n = 8) of transfer latency in seconds. One way ANOVA followed by Dunnett's test, P < 0.05,
*Positive control group was found to be significantly different than negative control group and
**Treatment groups were found significantly different than positive control group.

Effect of lutein on catalepsy was measured using standard bar test. Test was done at ten days interval. All values are expressed in cataleptic time in seconds.

| Time Interval in Mins. | Negative Control | Positive Control | A1 | A2 | B1 | B2 | C1 | C2 |
|---|---|---|---|---|---|---|---|---|
| | | | | Mean ± SEM secs. | | | | |
| | | | Effect of Lutein in Bar test on 1st Day | | | | | |
| 0 | 2.95 ± 0.3 | 2.38 ± 0.59 | 1.61 ± 0.37 | 2.08 ± 0.44 | 1.53 ± 0.22 | 1.65 ± 0.32 | 1.66 ± 0.17 | 1.74 ± 0.16 |
| 30 | 1.77 ± 0.21 | 2.38 ± 0.64 | 1.44 ± 0.26 | 2.92 ± 1.01 | 1.91 ± 0.21 | 1.9 ± 0.21 | 2.95 ± 1.32 | 2.33 ± 0.28 |
| 60 | 1.26 ± 0.166 | 1.81 ± 0.4 | 2.4 ± 0.59 | 3.02 ± 0.55 | 1.96 ± 0.22 | 1.68 ± 0.15 | 1.71 ± 0.09 | 2.27 ± 0.36 |
| 120 | 2.0 ± 0.48 | 1.35 ± 0.21 | 1.42 ± 0.33 | 3.83 ± 1.10 | 1.77 ± 0.12 | 1.78 ± 0.13 | 1.75 ± 0.21 | 1.82 ± 0.31 |
| 180 | 1.41 ± 0.19 | 2 ± 0.6 | 2.99 ± 0.99 | 2.86 ± 0.72 | 1.63 ± 0.16 | 1.64 ± 0.31 | 1.67 ± 0.16 | 2.11 ± 0.27 |
| 240 | 1.42 ± 0.18 | 2.89 ± 0.69 | 2.5 ± 0.63 | 4.43 ± 0.59 | 1.69 ± 0.11 | 1.87 ± 0.09 | 1.94 ± 0.14 | 1.53 ± 0.28 |
| | | | Effect of Lutein in Bar test on 10th Day | | | | | |
| 0 | 1.9 ± 0.59 | 2.62 ± 0.65 | 2.31 ± 0.73 | 2.27 ± 0.46 | 1.46 ± 0.04 | 1.35 ± 0.11 | 1.79 ± 0.22 | 1.88 ± 0.21 |
| 30 | 2.33 ± 0.61 | 2.61 ± 0.51 | 2.42 ± 0.33 | 2.42 ± 0.35 | 1.48 ± 0.12 | 1.65 ± 0.15 | 2.21 ± 0.27 | 2.09 ± 0.26 |
| 60 | 1.39 ± 0.55 | 1.95 ± 0.60 | 1.68 ± 0.57 | 1.32 ± 0.25 | 1.62 ± 0.13 | 1.61 ± 0.11 | 1.69 ± 0.16 | 1.94 ± 0.24 |
| 120 | 2.83 ± 0.65 | 1.91 ± 0.40 | 2.88 ± 0.64 | 2.73 ± 0.36 | 2.01 ± 0.26 | 1.60 ± 0.17 | 1.71 ± 0.14 | 2.01 ± 0.30 |
| 180 | 2.22 ± 0.50 | 1.91 ± 0.27 | 2.0 ± 0.2 | 2.72 ± 0.39 | 2.00 ± 0.13 | 1.92 ± 0.23 | 2.08 ± 0.16 | 2.11 ± 0.14 |
| 240 | 2.20 ± 0.35 | 2.17 ± 0.21 | 2.41 ± 0.43 | 1.98 ± 0.16 | 1.84 ± 0.25 | 1.88 ± 0.22 | 1.86 ± 0.32 | 2.03 ± 0.33 |
| | | | Effect of Lutein in Bar test on 20th Day | | | | | |
| 0 | 1.86 ± 0.54 | 12.3 ± 0.54* | 5.18 ± 0.31** | 4.57 ± 0.26** | 6.2 ± 0.48** | 7.14 ± 0.86** | 6.47 ± 0.55 | 6.70 ± 0.65 |
| 30 | 1.43 ± 0.34 | 10.68 ± 2.23* | 5.26 ± 1.91** | 5.52 ± 2.26** | 8.6 ± 0.87 | 6.80 ± 0.77** | 7.33 ± 0.41 | 7.23 ± 0.52 |
| 60 | 1.46 ± 0.37 | 8.58 ± 1.89* | 5.81 ± 1.97 | 7.23 ± 1.29 | 9.75 ± 1.32 | 9.71 ± 1.18 | 8.56 ± 1.44 | 8.67 ± 0.55 |
| 120 | 1.51 ± 0.3 | 14.68 ± 3.65* | 5.12 ± 2.53** | 5.83 ± 1.46** | 10.31 ± 0.8** | 8.33 ± 0.88** | 8.94 ± 0.55 | 10.32 ± 1.55 |
| 180 | 1.68 ± 0.63 | 18.01 ± 3.85* | 6.14 ± 1.55** | 10.84 ± 3.5** | 9.25 ± 0.73** | 9.17 ± 0.59** | 10.08 ± 1.10 | 9.77 ± 0.91 |
| 240 | 1.57 ± 0.62 | 18.60 ± 4.19* | 14.58 ± 3.49 | 10.3 ± 3.96** | 10.62 ± 0.83 | 9.29 ± 1.00 | 10.64 ± 0.62 | 8.62 ± 1.02 |

Data represents mean ± SEM (n = 8). One way ANOVA followed by Dunnett's test, P < 0.05,
*Positive control group was found to be significantly different than negative control group and
**Treatment groups were found significantly different than positive control group.

Brain Monoamine Estimations

Monoamine viz. Dopamine, Norepinephrine, 5-Hydroxytryptamine levels in brain were estimated at the end of the study. Animals were sacrificed and brains were removed to estimate the levels of neurotransmitters. All values are expressed in µg/g of brain weight.

Effect of Lutein on Brain Monoamine Levels

| Groups | Dopamine Mean ± SEM | Norepinephrine Mean ± SEM | 5-Hydroxytryptamine Mean ± SEM |
|---|---|---|---|
| NC | 0.97 ± 0.01* | 0.6 ± 0.05* | 0.58 ± 0.01* |
| PC | 0.49 ± 0.08 | 0.12 ± 0.02 | 0.23 ± 0.03 |
| A1 | 0.81 ± 0.12** | 0.39 ± 0.02** | 0.64 ± 0.14** |
| A2 | 0.69 ± 0.04** | 0.53 ± 0.01** | 0.47 ± 0.11** |
| B1 | 0.79 ± 0.15** | 0.49 ± 0.09** | 0.51 ± 0.18** |
| B2 | 0.86 ± 0.09** | 0.58 ± 0.12** | 0.49 ± 0.1** |
| C1 | 0.75 ± 0.17** | 0.42 ± 0.15** | 0.42 ± 0.08** |
| C2 | 0.89 ± 0.08** | 0.51 ± 0.07** | 0.55 ± 0.05** |

Data represents mean ± SEM (n = 8) expressed in µg/g of brain weight. One way ANOVA followed by Dunnett's test, P < 0.05,
*Positive control group was found to be significantly different than negative control and
**Treatment groups were found significantly different than positive control group.

DISCUSSION

Catalepsy (rigidity in movements), akinesia (slowing of movement), tremors and loss of memory are some of the major symptoms of Parkinson's disorder (P.D). Hence any molecule exhibiting anti-Parkinson's potential should be able to minimize or inhibit these symptoms of P.D. In the present study the effect of three samples containing Lutein in three different concentrations on catalepsy was evaluated by performing bar test. Bar test gives extent of catalepsy induced in the animal. Evaluation using bar test was done on 1st, 7th, 14th and 21st day of the study. The diseased control group was found to be significantly different from negative control i.e. the group of normal animals (P<0.05) at all the time intervals evaluated. All the groups treated with Lutein showed significant (P<0.05) anti-cataleptic activity as compared to the positive control. Lutein at both the dose levels (50 mg/kg and 100 mg/kg) and at all the provided concentrations exhibited significant anti-cataleptic activity.

In the present study water soluble composition of trans-lutein and zeaxanthin isomers (50 mg containing 2.5 mg of Lutein i.e. 5% Lutein) was then combined with different doses of Levodopa and Carbidopa. Different doses of Levodopa tried were 75, 50 and 25 mg/kg in combination with water soluble composition of trans-lutein and zeaxanthin isomers (50 mg containing 2.5 mg of Lutein i.e. 5% Lutein). In the study of the said doses on catalepsy, all combination treatment groups were found to be significantly different from positive control group. This indicates that the treatment with the water soluble composition of trans-lutein and zeaxanthin isomers (50 mg containing 2.5 mg of Lutein i.e. 5% Lutein) potentially reduced the dose levels of Levodopa and Carbidopa by three folds.

Akinesia is the hallmark symptom of P.D observed in almost all the patients of P.D. Effect of Lutein on locomotor activity of the haloperidol induced slowing of movements was evaluated using Actophotometer. This test was carried out on 5th, 10th, 15th and 20th day of the study. It is evident from the results that on 5th, 10th, and 15th day the positive control was significantly different (P<0.05) from negative control but there was no significant difference in locomotor activity of treatment groups and positive control group. It is clear from the results that on 20th day all the treatment groups are significantly different (P<0.05) from positive control group. Hence, it can be concluded that the effect of Lutein on locomotory changes improves on regular administration of Lutein.

While all combination treatments with Levodopa and Carbidopa significantly recovered ambulation counts as compared to the positive control group, Levodopa 75 mg/kg+Carbidopa 25 mg/kg+5% Lutein did not exhibit any significant difference as compared to negative control group but overall it differed significantly form Levodopa 50 mg/kg+Carbidopa 50 mg/kg+5% Lutein and Levodopa 25 mg/kg+Carbidopa 75 mg/kg+5% Lutein treated groups.

Effect of Lutein on learning and memory was evaluated by measuring transfer latency (TL) using elevated plus maze (EPM). Latency i.e. the time taken by the animal to enter into the closed arm of EPM was measured. TL was measured on 21st day of the study. It was observed that the animals in positive control group exceeded the cutoff time of 90 sec. While animals in negative control group entered in comparatively lesser time than that of positive control. Hence positive control showed significantly different ($P<0.05$) TL as compared to negative control. All the treatment groups showed significantly different ($P<0.05$) TL as compared to the positive control. In case of combination study groups, all treatment groups significantly recovered the transfer latency as compared to the positive control group.

Effect of Lutein on monoamine levels of brain was also evaluated at the 21st day of the study after sacrificing the animals. In P.D there is death of dopaminergic neurons and decreased levels of dopamine in brain is observed. Dopamine is an important neurotransmitter as far as body movements are concerned. Hence, Dopamine is the most important biomarker in P.D. Elevated or decreased levels of dopamine suggests the extent of P.D. Further Noradrenaline is concerned with the memory as in later stages of P.D nucleus cerelous which secretes noradrenaline gets damaged and hence noradrenaline levels were also measured. Besides this, the levels of all three monoamines are inter dependent on each other and hence the monoamine estimation was done.

In case of dopamine, noradrenaline and 5-hydroxytryptamine, positive control was significantly different ($P<0.05$) from negative control. In case of treatment groups significantly high levels of Dopamine, Noradrenaline and 5-hydroxytryptamine as compared to positive control group were observed. Hence, Lutein has potential of significantly elevating the levels of monoamines. Dopamine levels in brains of all combination treated groups were recovered significantly.

Lutein may act as an anti-Parkinson's agent at all the concentrations and at all the doses studied. The water soluble composition containing trans-lutein and zeaxanthin isomers (50 mg containing 2.5 mg Lutein i.e. 5% Lutein) shows 14.2 folds higher activity as compared to the concentrate containing high concentration of trans-lutein and zeaxanthin and 13.2 folds higher activity as compared to the concentrate containing trans-lutein and zeaxanthin isomers.

From the above data and results it is evident that the water soluble composition of trans-lutein and zeaxanthin isomers containing lower concentration of Lutein i.e. 5% Lutein exhibits similar or higher activity in prevention of Parkinson's disorder when compared with the concentrates containing high concentration of Lutein (i.e. 71% and 66% Lutein).

Combination studies with Levodopa and Carbidopa at different doses revealed that the combination of 5% Lutein 50 mg/kg with Levodopa 25 mg/kg and Carbidopa 6.25 mg/kg is better in all aspects showing potential against Parkinson's disorder with reduction in dose of Levodopa and Carbidopa.

We claim:

1. A method of treating Parkinson's disease, comprising:
    administering to an animal positive for Parkinson's disease an effective dose of a composition containing a molecular dispersion of carotenoids, the carotenoids consisting of lutein and zeaxanthin isomers, and the carotenoids being dispersed in a water soluble hydrophilic carrier, wherein the composition comprises at least 80% by weight of the carotenoids, and wherein the composition is safe for animal consumption, and as a dietary supplement; and
    administering to the animal positive for Parkinson's disease an effective dose of a therapeutic agent to treat Parkinson's disease,
    wherein the composition is administered in the range of 0.5 mg to 100 mg per day,
    wherein the therapeutic agents are carbidopa and levodopa,
    wherein levodopa is administered in the range of 25 mg to 75 mg per day,
    wherein carbidopa is administered in the range of 6.25 to 25 mg per day, and
    wherein the administering of the composition along with the administering of the therapeutic agent is effective to reduce the dose of the therapeutic agent to the animal positive with Parkinson's disease, relative to an animal positive with Parkinson's disease and administered with a higher dose of the therapeutic agent without administration of the composition.

2. The method of claim 1, wherein the composition further comprises a stabilizer.

3. The method of claim 2, wherein the composition further comprises a surfactant.

* * * * *